United States Patent [19]

Kamstra

[11] Patent Number: 4,529,403
[45] Date of Patent: Jul. 16, 1985

[54] AUTOMATIC INJECTION SYRINGE

[75] Inventor: Paulus R. Kamstra, Olst, Netherlands

[73] Assignee: Duphar International Research B.V., Weesp, Netherlands

[21] Appl. No.: 405,367

[22] Filed: Aug. 5, 1982

[30] Foreign Application Priority Data

Aug. 10, 1981 [NL] Netherlands .......................... 8103744

[51] Int. Cl.³ ............................................. A61M 5/20
[52] U.S. Cl. ..................................... 604/136; 604/191
[58] Field of Search .................. 604/134, 136, 89, 90, 604/82, 187, 191, 235, 238, 135; 206/528, 538

[56] References Cited

U.S. PATENT DOCUMENTS

| 2,591,046 | 4/1952 | Brown | 604/82 |
| 2,717,601 | 9/1955 | Brown | |
| 3,330,282 | 7/1967 | Visser et al. | |
| 3,881,484 | 5/1975 | Gidcumb, Jr. | 604/191 |
| 3,914,419 | 10/1975 | Haeger et al. | |
| 4,031,893 | 6/1977 | Kaplan et al. | 604/136 |
| 4,235,235 | 11/1980 | Bekkering | 604/238 |
| 4,394,863 | 7/1983 | Bartner | 604/191 |

FOREIGN PATENT DOCUMENTS

| 2110516 | of 1972 | France. |
| 871854 | 7/1961 | United Kingdom. |
| 1318803 | 5/1973 | United Kingdom. |
| 1449986 | 9/1976 | United Kingdom. |
| 2010681 | 7/1979 | United Kingdom. |

Primary Examiner—John D. Yasko
Attorney, Agent, or Firm—Stevens, Davis, Miller & Mosher

[57] ABSTRACT

The invention relates to an automatic syringe for injecting two or more different injection liquids which may not be in contact with each other for long periods of time. For that purpose, the ampoule between the piston and the needle connection includes one or more stoppers which keep the injection liquids separated from each other, while at a point a short distance before the needle connection a by-pass means is present through which the injection liquid or injection liquids present behind the stopper or stoppers can pass the stopper or stoppers during use of the syringe.

9 Claims, 7 Drawing Figures

AUTOMATIC INJECTION SYRINGE

The present invention relates to an automatic syringe for injecting two or more different injection liquids which may not be in contact with each other for extended periods of time, a so-called "plural injecting device".

In an automatic syringe, an ampoule and a hypodermic needle in operative association therewith is driven by the force of a power source so as to insert the needle and then inject the injection liquid present in the ampoule. Such a syringe comprises a combination of a discharge mechanism; a cartridge holder; and a cartridge which is slidably accomodated in the cartridge holder, and which comprises an ampoule, a piston which is movable in the ampoule and seals same, and a hypodermic needle which is connected to the front of the ampoule and, if desired, is covered by a flexible sheath to maintain the needle in a sterile condition. The discharge mechanism is provided with a power source which can move the cartridge from an inoperative condition to an operative condition. The syringe furthermore comprises locking means to control the actuation of the power source and preferably a safety device to block said locking means.

Automatic syringes have previously been developed, especially for use by persons who have to administer an injection into their own body at an instant which is not known beforehand. These persons include, for example, persons having an increased risk of a cardial infarct or soldiers after having been exposed to an enemy's battle gas, for example, a nerve gas. It should therefore be obvious that stringent requirements have to be imposed upon automatic syringes as regards the reliability and the ease of handling thereof. Such syringes are usually stored for years at a time and in addition are carried with the potential user under varying conditions for a long period of time. Moreover, operation of the syringe must be sufficiently ensured at the critical instant when an injection is required. When said critical moment has come, it must be possible to handle the syringe rapidly and easily, and to use the syringe in an efficacious manner. It may be desired, however, to be able to inject several medicaments at the critical instant which are not compatible during the storage period. In particular for military applications, the administration of several medicaments or antidotes is often necessary, for instance to reach an effective therapy, or because it is not known beforehand what type of battle gas will be used by the enemy. Said medicaments are often not compatible with each other during the long storage time of the syringe.

It is not advisable to use several automatic syringes filled with different injection liquids in the above-described emergency situation since there is a fair chance that a mistake may be made in choosing the correct syringes, it would take too long for all of the desired medicaments to be injected, and it is objectionable for a person to carry several syringes with him for a long period of time. Therefore, a single device is desired in which different injection liquids, which may not be in contact with each other for a long period of time, can be stored while separated from each other, but with which, if necessary, the injection liquids can be injected simultaneously or substantially simultaneously.

Such a syringe is known from U.S. Pat. No. 3,572,336. Injection liquids which are poorly compatible or are not at all compatible with each other can be injected simultaneously by means of the syringe described and shown in said Patent Specification. For that purpose, a number of medicament holders are in operative association with a number of needles or with one needle via a mixing chamber. A piston is present in each medicament holder, while the collective pistons are connected via separate piston rods to one common piston rod so that under the influence of a coiled spring the medicament holders can simultaneously be emptied. The syringe known from the above-mentioned United States Patent Specification is very complicated and hence less reliable than would be desired. In fact, the possibility of a component not operating satisfactorily, as a result of which the syringe would fail at the critical moment, becomes greater when the device comprises more components which are to give the desired result in cooperation with each other. In addition, the cost-price of such a complicated device will be high, as a result of which one may be inclined to replace the device less rapidly than is desirable; as a result of which the reliability of the system is also adversely influenced.

Another "plural injecting device" is known from European Patent Application 14006. The device described in said Application consists of a number of separate automatic single-compartment syringes which are assembled together in one outer casing in such manner that upon activation of one of the syringes the remaining syringes also become operative so that all of the injection liquids are simultaneously injected. This syringe is destined in particular for military application. The composition of enemy's battle gases varies regularly so that it is desired to replace from time to time in stored automatic syringes an antidote which is active against a given battle gas component. This can be done particularly easily in the "plural injecting device" known from the last-mentioned Patent Application, namely by simply replacing one of the single-compartment syringes therein with one having a different antidote. However, the disadvantage of the "plural injecting device" described in the above-mentioned Patent Application is the bulkiness and the weight of the syringe, as a result of which said syringe is less easy to carry and to use in case of need.

It is an object of the present invention to provide an automatic syringe for injecting two or more different injection liquids which may not be in contact with each other for a long period of time, which syringe must satisfy the following conditions: (1) easy handling, (2) reliability, and (3) simplicity of construction so that the cost of manufacture can be kept low. This object can be achieved by means of an automatic syringe comprising a combination of a discharge mechanism; a cartridge holder; and a cartridge which is slidably accomodated in the cartridge holder and which comprises an ampoule, a piston which is movable in the ampoule and seals same, and a hypodermic needle which is connected to the front of the ampoule, and, if desired, is covered by a sheath to maintain the needle in a sterile condition. The syringe according to the present invention is characterized in that the ampoule comprises, between the piston and the needle connection, one or more stoppers which are movable in the ampoule and which before use of the syringe keep the injection liquids present in the ampoule separated from each other since their circumferences adjoin the inner wall of the ampoule in a sealing manner. The syringe according to the present invention is also characterized in that the cartridge at a short distance before the needle connection includes a by-pass means past which the injection liquid or injection liquids present behind the stopper or stoppers can reach the cannula when during use of the syringe the stopper or stoppers is or are moved forward.

A very important additional advantage of the syringe according to the present invention is the flexibility of the liquid compartments. In the known syringes the volume of the liquid compartments are determined by the dimensions of the medicament holders, while the number of liquid compartments is entirely fixed once a given construction has been chosen. On the other hand, the volume of the liquid compartments of the syringe according to the present invention is fully variable because the distance between the piston and the stopper, between the stopper and the needle connection, and, if more stoppers are present, between the stoppers mutually, can be adjusted at will. The number of liquid compartments can also be chosen at will be varying the number of stoppers in the ampoule between piston and needle connection; only the length of the by-pass means must be adapted to the overall length of the collective stoppers.

In a preferred embodiment of the syringe according to the present invention, the needle is connected to the ampoule by means of a needle mount consisting of a collar provided on the front of the ampoule in a sealing manner, a neck in which the injection needle is connected and an entirely or substantially cylindrical shaft between collar and neck. A passage is formed in the inner wall of the shaft and the rear face of the neck, past which passage the injection liquid or injection liquids can reach the cannula when during use of the syringe the stopper or stoppers is or are moved into the shaft of the needle mount. Such a needle connection for a disposable prefilled single compartment syringe is described in Netherlands Patent Application 7714308 in the name of Applicants.

The by-pass means in the needle mount, between the inner wall of the shaft and the rear face of the neck on the one hand and the stopper or stoppers moved forward into the shaft on the other hand, as a result of which the injection liquid can reach the cannula, may be formed, for example, by one or more slots recessed in the inner wall of the shaft and the rear face of the neck and extending from the rear end of the shaft to the rear aperture of the cannula. The space bounded by the inner wall of the shaft and the rear face of the neck, apart from said slot or slots, has approximately the same diameter as the stopper or stoppers and is slightly longer than the stopper or the collective stoppers, so that the stopper or the collective stoppers in the extreme forward position can fill this space substantially entirely but does not or do not cover the end of said slot or slots adjoining the ampoule.

In another embodiment of the present invention, the rear face of the neck of the needle mount may be provided with a few spacing supports, while the space bounded by the inner wall of the shaft and the spacing supports on the rear face of the neck has a slightly larger circumference than the stopper or stoppers and is slightly longer than the stopper or the collective stoppers, so that the stopper or the collective stoppers in the extreme forward position can fill this room substantially entirely, in which, however, an aperture remains around the stopper or stoppers.

In still another embodiment of the present invention, the front face of the stopper nearest to the needle mount may comprise a few spacing supports, while the space bounded by the inner wall of the shaft and the rear face of the neck of the needle holder has a slightly larger circumference than the stopper or stoppers and is slightly longer than the stopper or the collective stoppers, including the spacing supports, so that the stopper or the collective stoppers in the extreme forward position can fill this space substantially entirely but in which an aperture remains around the stopper or stoppers.

As already explained, the number of liquid compartments in the syringe according to the present invention may be varied at will by providing more or fewer stoppers in the ampoule between the piston and the needle mount. When the length of the stoppers is fixed, the syringe according to the the above-described preferred embodiments of the present invention may simply be provided with a needle mount having a matching shaft length.

In another preferred embodiment of the automatic injection syringe of the present invention, the injection needle is connected to the front of the ampoule, while a passage is formed in the inner wall of the ampoule, past which passage the injection liquid or injection liquids can reach the cannula when during use of the syringe the stopper or stoppers is or are moved into a forward position. For this purpose the front of the ampoule may be narrowed so that a mouth or spout is formed wherein the needle is sealingly connected. Preferably, however, the needle is connected to the ampoule by means of a separate hub mounting the needle, or a needle mount. Such a needle mount is known e.g. from Netherlands patent application 7603511 in the name of the Applicants. A suitable needle mount consists of a sleeve made of plastic or of a suitable metal like aluminium. The rearward side of this sleeve is sealingly connected to the ampoule, e.g. by shrinking or folding around an outwardly extending flange at the front of the ampoule, while the forward side of the needle mount is narrowed to a hub or spout, wherein the needle is sealingly connected, e.g. by shrinking or folding. Such a needle mount is especially well suited for accomodating a membrane to prevent the foremost injection liquid from coming into contact with the metal of the cannula during storage of the syringe.

In this embodiment, the by-pass for the injection liquid or the injection liquids in the inner wall of the ampoule is formed by local deformation of the ampoule-wall between the needle connection or the membrane, if present, and the stopper, or, in the event more separating stoppers are present, the foremost stopper, over a length which is slightly larger than the length of the stopper or the collected stoppers. The local deformation is provided in such manner that a by-pass is formed through which upon actuation of the syringe the injection liquid or liquids behind the stopper or stoppers can reach the cannula past the stopper or stoppers.

The local deformation of the inner wall of the ampoule of the syringe according to the present invention may be made in various manners, for example, as is described in detail for a pre-filled disposable syringe in the non-prepublished Netherlands patent application 8103568 in the name of the Applicants. Preferably, the inner wall of the ampoule at the area of the deformation has one or more ridges which extend(s) in the longitudinal direction of the ampoule. Such ridge or ridges can very easily be provided as will be explained further. In another embodiment of the by-pass, the inner wall of the ampoule at the area of the deformation has an oval cross-section. In this case the inner wall of the ampoule at the area of the deformation may also comprise one or more slots, so that during use of the syringe the cannula is more accessible for the injection liquid or liquids. In still another embodiment of the by-pass, the ampoule at the area of the deformation is provided with one or more slots or channels which extend(s) in the longitudinal direction of the ampoule and is (are) slightly longer than the stopper or collected stoppers. In still another embodiment of the by-pass, the ampoule-wall is widened at the area of the deformation up to a diameter which is larger than that of the expanded stopper or stoppers, so that in the forward position of the stopper or stoppers the injection liquid behind the stopper or stoppers can pass substantially around the stopper or stoppers.

The wall of a glass ampoule can be locally deformed by locally heating the glass wall and depressing it to form one or more inward ridges, blowing it out to form one or more slots, or compressing it to an oval shape, with the aid of the known techniques available for this purpose. Local deformations of plastic ampoules can be achieved by using suitable moulds.

The injection liquid in the foremost compartment, i.e. the compartment before the stopper, or in the event more separating stoppers are present in the ampoule, the foremost stopper, is situated between this stopper and the rear end of the cannula or the needle connection. If it is undesirable to leave the injection liquid which is present in this compartment during storage of the syringe in contact with the metal of the injection needle, preferably a membrane should be sealingly provided behind the rear end of the cannula. Such a membrane is, for example, known from Netherlands patent application 6912907, and is preferably accomodated in the needle mount (see above). If there is a possibility that the stopper or foremost stopper may close the rear aperture of the cannula during actuation of the syringe, this stopper is preferably provided on its front side with spacing supports, e.g. three or four projections, or, alternatively, the rear face of the needle connecting means may be provided with spacing supports.

BRIEF DESCRIPTION OF THE DRAWINGS

The present invention will now be described in greater detail with reference to the preferred embodiments shown in the accompanying drawings, in which.

Figure 1:
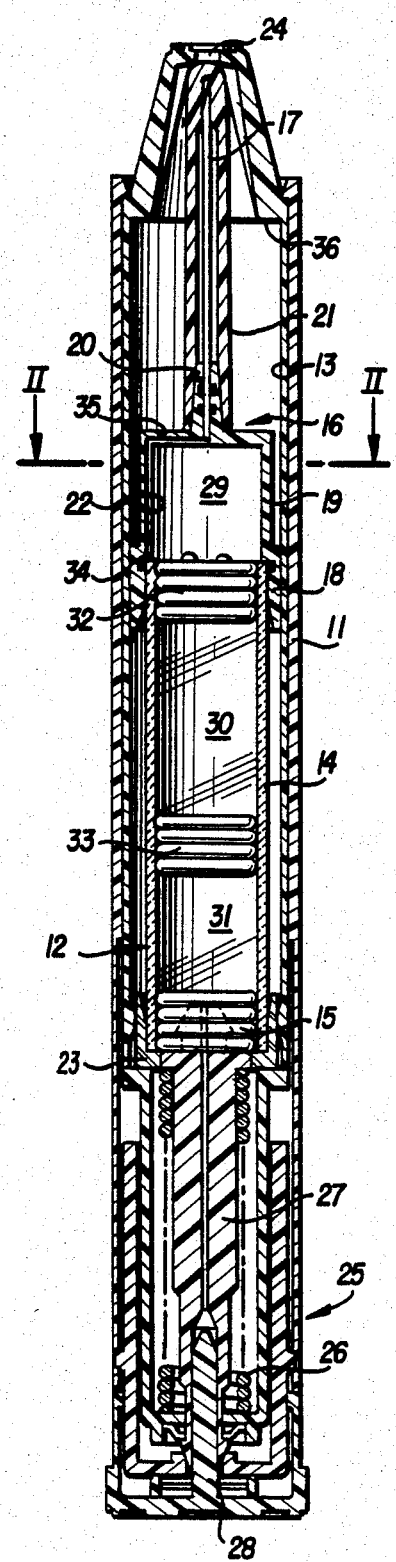
FIG. 1 is a longitudinal sectional view of a syringe according to the present invention in the condition in which it can be transported and stored.
Figure 2:
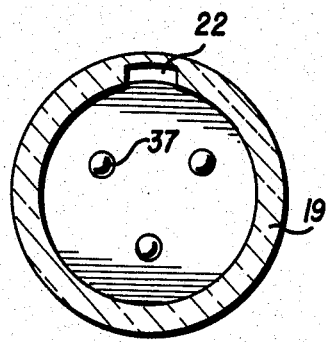
FIG. 2 is a cross-sectional view through the needle mount of the syringe of FIG. 1, namely taken on the line II—II of FIG. 1, viewed in the direction of the stopper.

The syringe shown in FIGS. 1 and 2 is constructed for the most part as described in detail and shown in Netherlands Patent Specification No. 160.725 in the name of Applicants. In general, the syringe comprises a cylindrical outer sleeve 11 in which a cartridge assembly 12 is provided so as to be slidable; said cartridge assembly comprising a cartridge holder sleeve or inner sleeve 13 fitting in the outer sleeve, a cylindrical glass ampoule 14 containing injection liquids, a piston 15 at one end and a needle mount 16 with injection needle 17 at the other end of the ampoule. At each end the ampoule comprises a radially outwardly projecting flange around which on the side of the injection needle the needle mount is connected by means of a collar 18. The needle holder furthermore comprises a shaft 19, which is cylindrical for the most part, and a neck 20 in which the needle 17 having a flexible needle guard 21 is connected. A slot or by-pass 22 is recessed in the inner wall of the shaft and the rear wall of the neck. An externally cylindrical sliding sleeve 23, which is slidable in the cartridge holder sleeve 13, is connected around the flange at the other end of the ampoule. The cartridge assembly 12 is provided in the outer sleeve 11 in such manner that the closed end of the needle guard 21 bears against the end of the cartridge holder sleeve 13 having a bore 24.

The outer sleeve 11 has a length such that the cartridge assembly 12 is accomodated in one end thereof and the discharge mechanism 25 is accomodated in the other end thereof. The discharge mechanism which, comprises a coil spring 26 as a power source is the same as the spring power assembly described in the above-mentioned Netherlands Patent Specification 160.725, and comprises locking means 27 and a safety device 28. Internally the ampoule 14 is divided into three separated liquid compartments 29, 30 and 31 by means of two cylindrical stoppers 32 and 33 which, like the piston, have a slightly larger diameter than the inside diameter of the ampoule. These stoppers, as well as the piston, are manufactured from a flexible material, preferably rubber of a pharmaceutical quality. The shaft of the needle mount, apart from the by-pass, has an inside diameter which is approximately equal to, but preferably slightly larger than that of the ampoule. Furthermore, the shaft of the needle mount is slightly longer than the two stoppers collectively, so that the end 34 of the by-pass adjoining the ampoule has just become uncovered when the stoppers are moved forward entirely to against the rear face of the neck of the needle mount.

When the syringe shown in FIGS. 1 and 2 is actuated, the cartridge assembly moves forward under the influence of the spring, the sliding sleeve 23 moving in the cartridge holder sleeve. The needle guard is compressed, the needle perforating the closed end of the needle guard and entering into the body at the point where the injection is to be administered. When the needle is in its foremost position, in which the needle mount is stopped when the front part 35 of the needle mount connecting the shaft and the neck abuts against a shoulder 36 formed by a constriction in the cartridge holder neck, the forward movement of the piston begins under the influence of the same spring, so that the actual injection is begun. The injection liquid in compartment 29 is now injected, the whole assembly of piston 15, stoppers 32 and 33 and liquid columns 30 and 31 moving forward. When the stopper 32 has moved in the shaft over a distance such that the rear of said stopper has passed the end 34 of the by-pass adjoining the tube, the injection liquid in compartment 30 can reach the cannula via the by-pass. When all the injection liquid from the compartments 29 and 30 has been injected, the front face of stopper 32 is positioned against the rear face of the neck of the needle mount and stoppers 32 and 33 bear against each other. At that instant, stopper 33 has moved forward over such a distance that the rear face of said stopper leaves the end 34 of the by-pass 22 adjoining the tube just uncovered so that the injection liquid in compartment 31 can also reach the cannula and can be injected.

Figure 3:
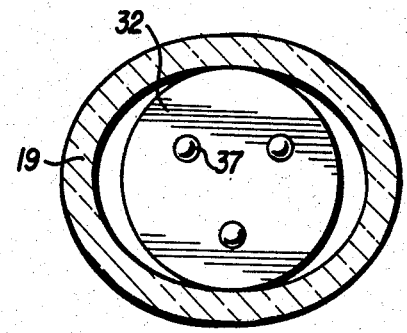
FIG. 3 is a cross-sectional view through the needle mount of a syringe taken along the same line as shown in FIG. 1, but this time of a different embodiment of the needle mount of the syringe in accordance with the present invention.

In another embodiment of the present invention the diameter of the shaft of the needle mount is slightly larger than that of the stoppers, so that the injection liquids behind the stoppers can pass the stoppers when they have been moved into the shaft. The shaft of the needle mount may have a circular or oval cross-section; the latter shape is shown in FIG. 3. The rear face of the neck of the needle mount or the front face of the front stopper comprises spacing supports, for example, in the form of caps or truncated cones. The cross-section shown in FIG. 3 is viewed in the direction of the front stopper 32, the front face of the stopper comprising three projections 37.

Figure 4:
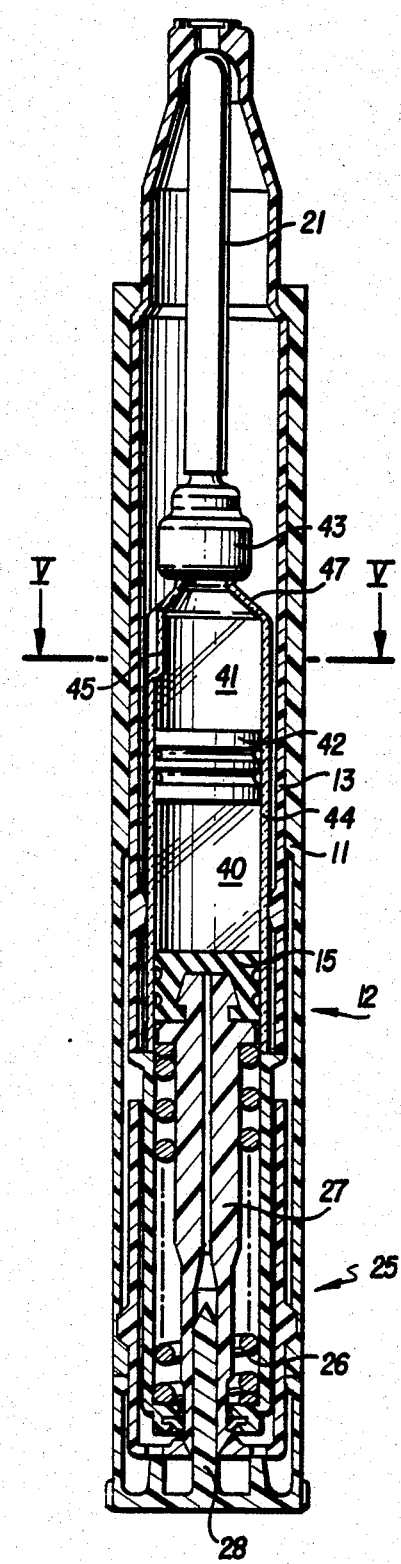
FIG. 4 shows a different embodiment of a syringe according to the present invention, partly in side-view and partly in longitudinal sectional view, in a condition wherein the syringe can be transported and stored.

The syringe shown in FIG. 4 comprises partially the same components as the syringe shown in FIG. 1. These equal parts have the same reference numbers, viz. outer sleeve 11, cartridge assembly 12, inner sleeve 13, piston 15, needle guard 21, discharge mechanism 25, coil spring 26, locking means 27 and safety device 28.

Internally the ampoule 44 of the syringe shown in FIG. 4 is divided into two separated liquid compartments 40 and 41 by means of a cylindrical rubber stopper 42, which has a slightly larger diameter than the inside diameter of the ampoule. The front of the ampoule is sealingly provided with an aluminium needle mount 43, the same as described in the before-mentioned Netherlands patent application 7603511; in this needle mount the needle is sealingly connected (not shown in the Figure). Behind the rear end of the cannula, and sealingly closing the liquid compartment 41 towards the cannula, a membrane is accomodated in the needle mount, the same as described in Netherlands patent application 6912907.

In front of the stopper 42, towards the needle connection, the wall of the ampoule is locally deformed. This deformation may have the form of a ridge 45 which extends internally in the longitudinal direction of the ampoule. This feature is more clearly visible in FIG. 5, which is a cross-sectional view through the ampoule of the syringe taken on the line V—V of FIG. 4, at the moment that the stopper 42 upon actuation of the syringe has been moved into the forward position. The ridge 45 is slightly longer than the stopper 42 and may be formed on the inner wall of the ampoule by locally heating the glass wall of the ampoule and depressing it. In another embodiment of the by-pass, the inner wall of the ampoule may be deformed by locally heating the wall of the ampoule and compressing it to an oval shape. As shown in FIG. 6, both the inner wall and the outer wall of the ampoule obtain an oval cross-section at the area of the deformation. This oval deformation of the ampoule should also be slightly longer than the length of the stopper. In still another embodiment shown in FIG. 7, the ampoule has a slot or channel 46 which extends in the longitudinal direction of the ampoule and which is slightly longer than the stopper, and through which the injection liquid behind the stopper can pass the stopper.

Figure 5:
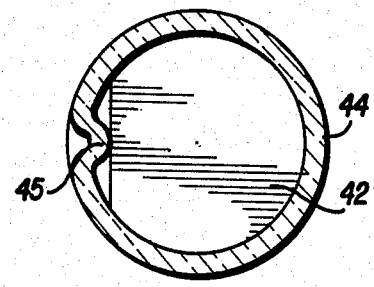
FIG. 5 is a cross-sectional view through the ampoule of the syringe of FIG. 4, namely taken on the line V—V of FIG. 4.
Figure 6:
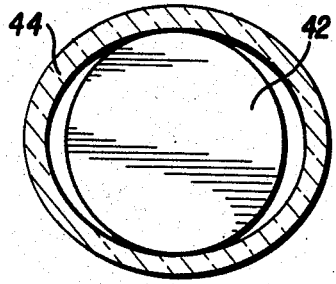
FIGS. 6 and 7 are cross-sectional views through the ampoule of a syringe taken along the same line as shown in FIG. 4, but in this case of different embodiments of the ampoule of a syringe according to the invention.
Figure 7:
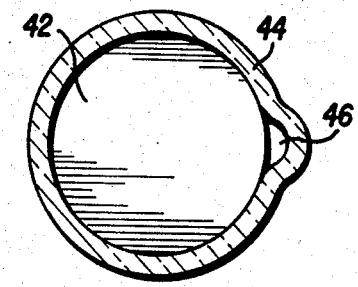

Of the embodiments presented in FIGS. 4 through 7, the by-pass shown in FIGS. 4 and 5 is to be preferred. This preference is based upon the fact that when using an ampoule provided with a by-pass as shown in FIGS. 4 and 5, the inner sleeve 13 does not need any adjustment, whereas, on the contrary, the by-passes shown in FIGS. 6 and 7 require a sleeve having an inner wall with an oval cross-section and a longitudinal recess respectively. Moreover, as opposed to the preferred by-pass shown in FIGS. 4 and 5, the assemblage, and especially the automatic assemblage, of the ampoule-containing cartridge into the inner sleeve is hindered by the asymmetrical cross-section of the inner sleeve in case of the by-passes shown in FIGS. 6 and 7.

In general, the actuation of the syringe shown in FIGS. 4 through 7 is the same as described for the embodiments shown in FIGS. 1 through 3. After rupture of the membrane, the injection liquid in compartment 41 is expelled through the cannula. Meanwhile, the stopper 42 is pushed forward under the influence of the spring force until it abuts against a shoulder 47 of the ampoule 44. As a result of the deformation of the stopper, small ducts are formed on either side of the ridge 45 (see FIG. 5). The injection liquid present in compartment 40 can pass the stopper via the ducts and can thus reach the cannula and be expelled. In the embodiments of the by-pass shown in FIGS. 6 and 7, the injection liquid in compartment 40 can equally pass the stopper at the area of the widening of the ampoule wall.

When the injection liquid between stopper and piston has been expelled as completely as possible, the front of the piston contacts the rear side of the stopper. It will be obvious that the front of the piston and the rear side of the stopper are substantially complementary and are preferably substantially flat faces in order to keep the residual volume of injection liquid as small as possible.

I claim:
1. An automatic syringe for injecting two or more different liquids which may not be in contact with each other for long periods of time, comprising:
 a combination of a discharge mechanism; a cartridge holder; and a cartridge slidably accomodated in the holder, said cartridge comprising:
 an ampoule; a piston which is movable in the ampoule and seals same; and a hypodermic needle connected to the ampoule by means of a needle mount, said needle mount comprising:
 a collar connected to the front of the ampoule in a sealing manner; a neck in which the injection needle is connected; and an entirely or substantially cylindrical shaft between the collar and the neck,
 said syringe being characterized in that the ampoule includes at least one stopper between the piston and the needle mount, said stopper being movable in the ampoule and having a circumference that adjoins the inner wall of the ampoule in a sealing manner, thereby keeping the injection liquids separated from each other prior to use of the syringe;
 said syringe being further characterized in that the cartridge includes a by-pass means through which the injection liquid or injection liquids present behind the stopper or stoppers can reach the needle when during use of the syringe the stopper or stoppers is or are moved into the shaft of the needle mount, said by-pass means comprising at least one slot extending from the rear of the shaft to the rear aperture of the needle, said slot being recessed in the inner wall of the shaft and the rear face of the neck;

said syringe being still further characterized in that the space bounded by the inner wall of the shaft and the rear face of the neck, apart from said slot, has approximately the same diameter as the stopper and is slightly longer than the stopper or collection of stoppers, so that the stopper or collection of stoppers in the extreme forward position can substantially entirely fill said space but does not or do not cover the end of the slot or slots adjoining the ampoule.

2. An automatic syringe for injecting two or more different liquids which may not be in contact with each other for long periods of time, comprising:

a combination of a discharge mechanism; a cartridge holder; and a cartridge slidably accomodated in the holder, said cartridge comprising:

an ampoule; a piston which is movable in the ampoule and seals same; and a hypodermic needle connected to the ampoule by means of a needle mount, said needle mount comprising:

a collar connected to the front of the ampoule in a sealing manner; a neck in which the injection needle is connected; and an entirely or substantially cylindrical shaft between the collar and the neck, said syringe being characterized in that the ampoule includes at least one stopper between the piston and the needle mount, said stopper being movable in the ampoule and having a circumference that adjoins the inner wall of the ampoule in a sealing manner, thereby keeping the injection liquids separated from each other prior to use of the syringe;

said syringe being further characterized in that the cartridge includes a by-pass means through which the injection liquid or injection liquids present behind the stopper or stoppers can reach the needle when during use of the syringe the stopper or stoppers is or are moved into the shaft of the needle mount, said by-pass means comprising a passage formed in the inner wall of the shaft and the rear face of the neck;

said syringe being still further characterized in that the rear face of the neck of the needle mount includes a plurality of spacing supports, and in that the space bounded by the inner wall of the shaft and the spacing supports on the rear face of the neck has a slightly larger circumference than the stopper and is slightly longer than the stopper or collection of stoppers, so that the stopper or collection of stoppers in the extreme forward position can substantially entirely fill said space, but in which an aperture remains around the stopper or stoppers.

3. An automatic syringe for injecting two or more different liquids which may not be in contact with each other for long periods of time, comprising:

a combination of a discharge mechanism; a cartridge holder; and a cartridge slidably accomodated in the holder, said cartridge comprising:

an ampoule; a piston which is movable in the ampoule and seals same; and a hypodermic needle connected to the ampoule by means of a needle mount, said needle mount comprising:

a collar connected to the front of the ampoule in a sealing manner; a neck in which the injection needle is connected; and an entirely or substantially cylindrical shaft between the collar and the neck, said syringe being characterized in that the ampoule includes at least one stopper between the piston and the needle mount, said stopper being movable in the ampoule and having a circumference that adjoins the inner wall of the ampoule in a sealing manner, thereby keeping the injection liquids separated from each other prior to use of the syringe;

said syringe being further characterized in that the cartridge includes a by-pass means through which the injection liquid or injection liquids present behind the stopper or stoppers can reach the needle when during use of the syringe the stopper or stoppers is or are moved into the shaft of the needle mount, said by-pass means comprising a passage formed in the inner wall of the shaft and the rear face of the neck;

said syringe being still further characterized in that the front face of the stopper nearest to the needle mount or the rear face of the neck of the needle mount includes a plurality of spacing supports, and in that the space bounded by the inner wall of the shaft and the rear face of the neck of the needle mount has a slightly larger circumference than the stopper and is slightly longer than the stopper or collection of stoppers, including the spacing supports, so that the stopper or collection of stoppers in the extreme forward position can substantially entirely fill said space, but in which an aperture remains around the stopper or stoppers.

4. An automatic syringe for injecting two or more different liquids which may not be in contact with each other for long periods of time, comprising:

a combination of a discharge mechanism; a cartridge holder; and a cartridge slidably accommodated in the holder, said cartridge comprising:

an ampoule; a piston which is movable in the ampoule and seals same; and a hypodermic needle connected to the ampoule by means of a needle mount and, if desired, covered by a flexible sheath to maintain the needle in a sterile condition, said needle mount comprising:

a collar connected to the front of the ampoule in a sealing manner and maintaining the ampoule in radially spaced relationship from said holder; a neck in which the injection needle is connected; and an entirely or substantially cylindrical shaft between the collar and the neck;

said syringe being characterized in that said cartridge includes said injection liquids and said ampoule includes at least one stopper between the piston and the needle mount, said stopper being movable in the ampoule and having a circumference that adjoins the inner wall of the ampoule in a sealing manner, thereby keeping the injection liquids separated from each other prior to use of the syringe;

said syringe being further characterized in that the cartridge includes a by-pass means through which the injection liquid or injection liquids present behind the stopper or stoppers can reach the needle past the stopper or stoppers when during use of the syringe the stopper or stoppers is or are moved into the shaft of the needle mount, said by-pass means comprising means in said shaft for cuasing said stopper or stoppers to move out of sealed relationship with said shaft, said means extending longitudinally for a distance slightly greater than the length of the stopper or collection of stoppers.

5. A syringe as claimed in claim 4, wherein the inner surface of said holder is substantially cylindrical over substantially the entire length travelled by said cartridge upon activation of said syringe.

6. An automatic syringe as claimed in any one of claims 1, 2 or 3, wherein said cartridge includes said injection liquids.

7. An automatic syringe for injecting two or more different liquids which may not be in contact with each other for long periods of time, comprising:
   a combination of a discharge mechanism; a cartridge holder; and a cartridge slidably accommodated in the holder, said cartridge comprising:
   an ampoule; a piston which is movable in the ampoule and seals same; and a hypodermic needle connected to the front of the ampoule,
   said syringe being characterized in that the ampoule includes at least one stopper between the piston and the needle mount, said stopper being movable in the ampoule and having a circumference that adjoins the inner wall of the ampoule in a sealing manner, thereby keeping the injection liquids separated from each other prior to use of the syringe;
   said syringe being further characterized in that the cartridge includes a by-pass means, said by-pass means comprising at least one radially inwardly directed ridge on the inner wall of the ampoule extending in the longitudinal direction of the ampoule, between the needle connection and the stopper or foremost stopper, said ridge being of a length which is slightly greater than the length of the stopper or collection of stoppers and in a manner such that upon actuation of the syringe a by-pass is formed through which the injection liquid or injection liquids present behind the stopper or stoppers can reach the needle past the stopper or stoppers.

8. An automatic syringe for injecting two or more different liquids which may not be in contact with each other for long periods of time, comprising:
   a combination of a discharge mechanism; a cartridge holder; and a cartridge slidably accommodated in the holder, said cartridge comprising:
   an ampoule; a piston which is movable in the ampoule and seals same; and a hypodermic needle connected to the front of the ampoule,
   said syringe being characterized in that the ampoule includes at least one stopper between the piston and the needle mount, said stopper being movable in the ampoule and having a circumference that adjoins the inner wall of the ampoule in a sealing manner, thereby keeping the injection liquids separated from each other prior to use of the syringe;
   said syringe being further characterized in that the cartridge includes a by-pass means, said by-pass means comprising an oval cross-section in he inner wall of the ampoule between the needle connection and the stopper or foremost stopper, said oval cross-section extending over a length which is slightly greater than the length of the stopper or collection of stoppers and in a manner such that upon actuation of the syringe a by-pass is formed through which the injection liquid or injection liquids present behind the stopper or stoppers can reach the needle past the stopper or stoppers.

9. An automatic syringe for injecting two or more different liquids which may not be in contact with each other for long periods of time, comprising:
   a combination of a discharge mechanism; a cartridge holder; and a cartridge slidably accommodated in the holder, said cartridge comprising:
   an ampoule; a piston which is movable in the ampoule and seals same; and a hypodermic needle connected to the front of the ampoule,
   said syringe being characterized in that the ampoule includes at least one stopper between the piston and the needle mount, said stopper being movable in the ampoule and having a circumference that adjoins the inner wall of the ampoule in a sealing manner, thereby keeping the injection liquids separated from each other prior to use of the syringe;
   said syringe being further characterized in that the cartridge includes a by-pass means, said by-pass means comprising a wider diameter for the inner wall of the ampoule between the needle connection and the stopper or foremost stopper than the diameter of the remainder of said ampoule, said wider diameter extending over a length which is slightly greater than the length of the stopper or collection of stoppers and in a manner such that upon actuation of the syringe a by-pass is formed through which the injection liquid or injection liquids present behind the stopper or stoppers can reach the needle past the stopper or stoppers.

* * * * *